United States Patent [19]

Day

[11] 4,212,819
[45] * Jul. 15, 1980

[54] PROCESS FOR THE PREPARATION OF BENZOYL HALIDE AND HALOSULFONYLBENZOYL HALIDE

[75] Inventor: F. Howard Day, Grand Island, N.Y.

[73] Assignee: Hooker Chemicals & Plastics Corp., Niagara Falls, N.Y.

[*] Notice: The portion of the term of this patent subsequent to Aug. 29, 1995, has been disclaimed.

[21] Appl. No.: 923,411

[22] Filed: Jul. 10, 1978

Related U.S. Application Data

[63] Continuation-in-part of Ser. No. 839,045, Oct. 3, 1977, Pat. No. 4,110,373.

[51] Int. Cl.$^2$ .................. C07C 51/58; C07C 63/10; C07C 143/38; C07C 143/40
[52] U.S. Cl. .................. 260/543 R; 260/543 F; 260/544 D; 260/544 S
[58] Field of Search ........... 260/543 R, 544 D, 544 S, 260/543 F

[56] References Cited

U.S. PATENT DOCUMENTS

| | | | |
|---|---|---|---|
| 3,290,370 | 12/1966 | Weil et al. | 260/544 |
| 3,322,822 | 5/1967 | Gelfand | 260/544 |
| 4,110,373 | 8/1978 | Day | 260/543 R |

OTHER PUBLICATIONS

Chemical Abstract, vol. 29, 5090$^2$ (1935).
Groggins, "Unit Processes in Organic Synthesis" p. 268 (1952).

Primary Examiner—Paul J. Killos
Attorney, Agent, or Firm—Peter F. Casella; William J. Crossetta, Jr.; Arthur S. Cookfair

[57] ABSTRACT

A process for the preparation of benzoyl halide and meta-halosulfonyl benzoyl halide comprises adding to sulfuric acid and reacting therewith a benzotrihalide compound characterized by the formula:

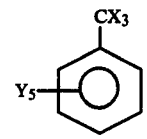

wherein X is bromine or chlorine and Y is individually selected from the group consisting of fluorine, chlorine, bromine, iodine, alkyl, preferably of one to six carbon atoms, halosubstituted alkyl, preferably trichloromethyl or tribromomethyl, aryl, preferably phenyl, and hydrogen, with the proviso that at least one Y substituent at a meta position is hydrogen.

9 Claims, No Drawings

PROCESS FOR THE PREPARATION OF BENZOYL HALIDE AND HALOSULFONYLBENZOYL HALIDE

This application is a continuation-in-part of Ser. No. 839,045, filed Oct. 3, 1977 now U.S. Pat. No. 4,110,373.

BACKGROUND OF THE INVENTION

This invention relates to an improved process for the preparation of benzoyl halides and meta-halosulfonylbenzoyl halides and, more particularly, to such process involving the reaction of benzotrihalide with sulfuric acid.

Benzoyl halides and chlorosulfonylbenzoyl halides are well known in the chemical industry and have been employed in as intermediates for a variety of known and useful end products. Benzoyl halides, are highly reactive acid halides, useful in a variety of reactions to introduce the benzoyl group into organic compounds, especially through Friedel-Crafts reactions. Benzoyl halides are employed in the preparation of perfumes, pharmaceuticals, dyes, resins and pesticides. Similarly, halosulfonylbenzoyl halides are known to be useful for a variety of purposes and have been employed, for example, as polymerization catalysts and as intermediates in the preparation of pharmaceuticals and azo dyes. In addition, meta-halosulfonylbenzoyl halides, may be desulfonylated in a known manner to prepare m-halobenzoyl halides, which, in turn, are useful for various purposes in the chemical industry, including, for example, as chemical intermediates for the preparation of dyes; pharmaceuticals; agricultural chemicals; as well as various other organic chemical end products.

Various methods for the preparation of benzoyl halides or meta-sulfonylbenzoyl halides are known in the art. It is known, for example, from U.S. Pat. No. 3,691,217, that benzoyl chlorides and benzaldehydes may be produced by reacting benzo polychloromethanes, such as benzotrichloride, with an organic carboxylic acid in the presence of a tin chloride catalyst.

U.S. Pat. No. 3,290,370, to Weil and Lisanke, disclose the preparation of m-chlorosulfonylbenzoyl chloride by reaction of benzotrichloride with chlorosulfonic acid. The stoichiometry of the reaction is such that, even under ideal conditions, for each mole of desired product, two moles of mineral acid are produced, with the need for disposal thereof. In addition, to obtain high yields of the desired m-chlorosulfonylbenzoyl chloride, substantial excess of the chlorosulfonic acid is employed, presenting additional problems of separation, and disposal or recycling thereof.

U.S. Pat. No. 3,322,822 to Gelfand, discloses the preparation of m-chlorosulfonylbenzoyl chloride by reaction of benzotrichloride and sulfur trioxide. With the use of substantial excess of sulfur trioxide reactant, yields of m-chlorosulfonylbenzoyl chloride as high as 65% are shown to be obtainable.

Although the prior art provides a variety of processes for the preparation of either benzoyl halides or halosulfonylbenzoyl halides, it will be appreciated that still further improvements in efficient utilization of reactants is desirable as well as improvements in the yield of the meta-isomer of halosulfonylbenzoyl halide obtainable.

Accordingly, it is an object of this invention to provide an improved process for the preparation of halosulfonylbenzoyl halides wherein the meta-isomer thereof may be selectively produced in high yields. It is a further object to provide a process for the preparation of co-products, benzoyl halides and halosulfonylbenzoyl halides wherein the proportional yield of each may be controllably varied.

SUMMARY OF THE INVENTION

This invention provides a process for the co-production of benzoyl halides and m-halosulfonylbenzoyl halides by reaction of sulfuric acid with a benzotrihalide compound of the formula:

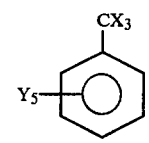

wherein X is bromine or chlorine and Y is individually selected from the group consisting of hydrogen, fluorine, chlorine, bromine, iodine, alkyl, halosubstituted alkyl, and aryl, with the proviso that at least one Y substituent at a meta position is hydrogen. In the above formula, the preferred alkyl group represented by Y are those of one to six carbon atoms and the preferred haloalkyl groups are chloroalkyl and bromoalkyl of one to six carbon atoms, and most preferably trichloromethyl or tribromomethyl. The preferred aryl substituents are phenyl or substituted phenyl wherein electron-withdrawing substituents, such as nitro- or tri-halomethyl, are present on the ring.

The process is carried out by addition of the benzotrihalide to sulfuric acid. The co-products prepared in this manner are benzoyl halides and meta-halosulfonylbenzoyl halides characterized, respectively by the formulas:

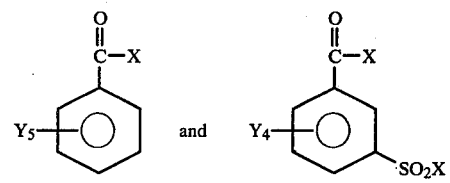

wherein Y is as defined herein above.

DESCRIPTION OF PREFERRED EMBODIMENTS

The preferred benzotrihalide starting materials are benzotrichloride compounds characterized by the formula:

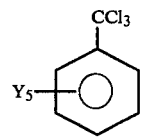

wherein Y is chlorine or hydrogen; especially benzotrichloride and o-chloro,-m-chloro-, and p-chlorobenzotrichloride. These compounds are reacted with sulfuric acid, in accordance with the process of this invention, to prepare correspondingly substituted benzoyl chlorides and m-chlorosulfonylbenzoyl chlorides. Thus, when benzotrichloride is employed as the starting material, the co-products obtained by the process of this invention will be benzoyl chloride and m-chlorosulfonylbenzoyl chloride. Utilizing p-chlorobenzotrichloride as the starting material results in the co-production of p-chloro-benzoyl chloride and 4-chloro-3-chlorosulfonylbenzoyl chloride. Starting with m-chlorobenzotrichloride yields, as co-products, m-chloro-benzoyl chloride and 5-chloro-3-chlorosulfonylbenzoyl chloride.

The use of sulfuric acid as a sulfonating agent in the process of this invention provides specific advantages in terms of the high yield of meta-isomer obtained in the halosulfonylbenzoyl halide product and, in addition, provides an advantageous degree of control over the proportional yield of the co-products obtained. It has been found that the proportional yield of co-products may be predictably varied, depending on the composition of the sulfuric acid reactant. In general, the higher the strength of the sulfuric acid employed (and thus the lower the amount of water present), the higher the proportion of m-halosulfonylbenzoyl halide that will be produced. Conversely, the greater the amount of water present (i.e. the weaker the sulfuric acid), the higher the proportion of benzoyl halide that will be produced. Thus, by controlling the strength of the sulfuric acid reactant, the proportion of co-products may be varied accordingly.

It has been found that when benzotrihalide is sulfonated in accordance with this invention, the use of sulfuric acid of lower strength, such as about 50 to about 75% will result in increased proportion of benzoyl halide produced whereas the use of sulfuric acid of higher strength, such as 75 to about 100% sulfuric acid, will result in an increase in the proportion of halosulfonylbenzoyl halide produced. The advantage of such controllable variation of co-products resides in the ease with which the process may be varied to increase or decrease the proportional yield of either co-product, depending on market needs, economic factors or other considerations prevailing at any given time. In a preferred embodiment of the invention, where it is desired to maximize the production of halosulfonylbenzoyl halide and especially the meta-isomer thereof, it is preferred to employ a sulfuric acid composition of about 90 to about 100 percent sulfuric acid.

The temperature at which the process of this invention may be carried out, under atmospheric conditions, may vary considerably, for example from temperatures as low as about 20° or lower to as high as 200° Celsius or higher. Temperatures as low as the freezing point of the sulfuric acid reactant may be employed, however, such lower temperatures provide no advantage and thus are not preferred. Similarly, higher temperatures, such as above about 200° Celsius are not preferred since an increase in undesirable residues may result.

The preferred temperature at which the present process is carried out is from about 50° to about 200° Celsius, and most preferably about 80° to about 180° Celsius.

The temperature considerations suggested are premised on the basis of a reaction at about atmospheric pressure. Sub-atmospheric pressures may be employed but are not preferred. Super-atmospheric pressures may be employed with appropriate changes in preferred temperatures in accordance with the vapor pressure changes resulting from such pressure increase.

It has been found particularly advantageous to carry out the process of this invention by the gradual addition of the benzotrihalide to the sulfuric acid sulfonating agent and proceeding in this manner as the sulfonating agent is consumed. The gradual addition of the benzotrihalide may be continuous or intermittant. Utilizing this order of addition, it has been found that undesirable side reactions may be substantially avoided. In addition, the reaction may be continued in this manner until substantially all of the sulfonating agent and water present is consumed. In practice, an excess of benzotrihalide may be added. thus allowing substantially complete utilization of the sulfonating agent.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A reaction vessel, equipped with a reflux condenser, thermometer, external temperature control means, and stirring means, was charged with 51.6 parts of 95–98% $H_2SO_4$ and heated to about 150° C. A total of 223.5 parts of benzotrichloride was added slowly over a period of 3.7 hours, during which time the reaction temperature was maintained at about 150° C. Following the addition of benzotrichloride the temperature was maintained at about 150° C., with stirring for an additional hour. The reaction mixture was then distilled at reduced pressure to yield 91.3 parts of a first fraction containing about 90% benzoyl chloride and a second fracation of 106.3 parts of m-chlorosulfonylbenzoyl chloride. Analysis of the m-chlorosulfonylbenzoyl chloride produce indicated approximately 95.2% meta-isomer; 0.06 ortho-isomer; and 4.8% para-isomer.

In a similar manner, following the general procedure of the foregoing example, substituted benzotrihalides are reacted with sulfuric acid to yield substituted benzoyl chlorides and substituted m-halosulfonylbenzoyl halides.

What is claimed is:

1. A process for the co-production of benzoyl halide and meta-halo-sulfonylbenzoyl halide by the reaction of benzotrihalide with sulfuric acid which comprises gradually adding to sulfuric acid, a benzotrihalide of the formula:

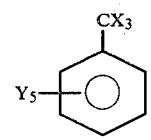

wherein X is bromine or chlorine and Y is individually selected from the group consisting of fluorine, chlorine, bromine, iodine, alkyl, halo-substituted alkyl, aryl, and hydrogen, with the proviso that at least one Y substituent at a meta-position is hydrogen.

2. A process according to claim 1 wherein X is chlorine.

3. A process according to claim 1 wherein the benzotrihalide is characterized by the formula:

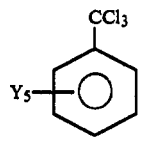

wherein Y is chlorine or hydrogen.

4. A process according to claim 1 wherein the benzotrihalide is benzotrichloride.

5. A process according to claim 1 wherein the sulfuric acid is about 50 to about 100 percent sulfuric acid.

6. A process according to claim 5 wherein the reaction is maintained at a temperature of about 20° to about 200° Celsius.

7. A process according to claim 6 wherein the sulfuric acid is about 50 to about 75 percent sulfuric acid.

8. A process according to claim 6 wherein the sulfuric acid is about 75 to about 100 percent sulfuric acid.

9. A process for the production of benzoyl chloride and m-chlorosulfonylbenzoyl chloride by the reaction of benzotrichloride with sulfuric acid, which comprises gradually adding the benzotrichloride to a sulfuric acid reaction medium having an initial composition of about 90 to about 100 percent sulfuric acid and maintaining the temperature of the reaction medium in the range of about 80° to about 180° Celsius.

* * * * *